US00PP25243P2

(12) United States Plant Patent
Noordhuis

(10) Patent No.: US PP25,243 P2
(45) Date of Patent: Jan. 20, 2015

(54) ***RUDBECKIA* PLANT NAMED 'ET-RDB 02'**

(50) Latin Name: *Rudbeckia hirta×Echinacea purpurea*
Varietal Denomination: ET-RDB 02

(71) Applicant: Bart Noordhuis, Boijl (NL)

(72) Inventor: Bart Noordhuis, Boijl (NL)

(73) Assignee: Eternal Plant Boijl B.V., Boijl (NL)

( * ) Notice: Subject to any disclaimer, the term of this patent is extended or adjusted under 35 U.S.C. 154(b) by 87 days.

(21) Appl. No.: 13/815,474

(22) Filed: Mar. 5, 2013

(51) Int. Cl.
*A01H 5/00* (2006.01)

(52) U.S. Cl.
USPC ..... Plt./474

(58) Field of Classification Search
USPC ..... Plt./474
See application file for complete search history.

*Primary Examiner* — Annette Para
(74) *Attorney, Agent, or Firm* — C. A. Whealy

(57) ABSTRACT

A new and distinct cultivar of *Rudbeckia* plant named 'ET-RDB 02', characterized by its compact, upright to outwardly spreading and mounded plant habit; freely branching growth habit; relatively small leaves; freely flowering habit; single-type inflorescences with yellow, orange and reddish-colored ray florets and dark purple-colored disc florets positioned above the foliar plane on strong peduncles; and good post-production longevity.

2 Drawing Sheets

Botanical designation: *Rudbeckia hirta×Echinacea purpurea.*
Cultivar denomination: 'ET-RDB 02'.

CROSS REFERENCED TO CLOSELY-RELATED APPLICATIONS

Title: *Rudbeckia* Plant Named 'ET-RDB 01'
Applicant: Bart Noordhuis
U.S. Plant patent application Ser. No. 13/815,479.

BACKGROUND OF THE INVENTION

The present invention relates to a new and distinct cultivar of *Rudbeckia* plant, botanically known as *Rudbeckia hirta× Echinacea purpurea* and hereinafter referred to by the name 'ET-RDB 02'.

The new *Rudbeckia* plant is a product of a planned breeding program conducted by the Inventor in Boijl, The Netherlands. The objective of the breeding program is to create new compact *Rudbeckia* plants with small leaves and attractive long-lasting inflorescences.

The new *Rudbeckia* plant originated from a cross-pollination made by the Inventor in Boijl, The Netherlands in 2010 of a proprietary selection of *Rudbeckia hirta* identified as code number 7-357, not patented, as the female, or seed parent with a proprietary selection of *Echinacea purpurea* identified as code number 124-6, not patented, as the male, or pollen, parent. The new *Rudbeckia* plant was discovered and selected by the Inventor as a single flowering plant from within the progeny of the stated cross-pollination in a controlled environment in Boijl, The Netherlands in 2011.

Asexual reproduction of the new *Rudbeckia* by tissue culture in a controlled greenhouse environment in Boijl, The Netherlands since 2011 has shown that the unique features of this new *Rudbeckia* are stable and reproduced true to type in successive generations.

SUMMARY OF THE INVENTION

Plants of the new *Rudbeckia* have not been observed under all possible environmental conditions and cultural practices.

The phenotype may vary somewhat with variations in environmental conditions such as temperature and light intensity, without, however, any variance in genotype.

The following traits have been repeatedly observed and are determined to be the unique characteristics of 'ET-RDB 02'. These characteristics in combination distinguish 'ET-RDB 02' as a new and distinct *Rudbeckia* plant:

1. Compact, upright to outwardly spreading and mounded plant habit.
2. Freely branching growth habit.
3 Relatively small leaves.
4. Freely flowering habit.
5. Single-type inflorescences with yellow, orange and reddish-colored ray florets and dark purple-colored disc florets positioned above the foliar plane on strong peduncles.
6. Good postproduction longevity.

Plants of the new *Rudbeckia* differ from plants of the female parent selection in the following characteristics:

1. Plants of the new *Rudbeckia* are more compact and denser than plants of the female parent selection.
2. Inflorescences of plants of the new *Rudbeckia* are longer lasting than inflorescences of plants of the female parent selection.

Plants of the new *Rudbeckia* differ from plants of the male parent selection in the following characteristics:

1. Plants of the new *Rudbeckia* are more compact and denser than plants of the male parent selection.
2. Inflorescences of plants of the new *Rudbeckia* are longer lasting than inflorescences of plants of the male parent selection.

Plants of the new *Rudbeckia* can be compared to *Rudbeckia hirta×Echinacea purpurea* 'ET-RDB 01', disclosed in a U.S. Plant patent application Ser. No. 13/815,479. Plants of the new *Rudbeckia* differ primarily from plants of 'ET-RDB 01' in the following characteristics:

1. Plants of the new *Rudbeckia* are taller than plants of 'ET-RDB 01'.

2. Plants of the new *Rudbeckia* have more ray florets per inflorescence than plants of 'ET-RDB 01'.
3. Plants of the new *Rudbeckia* and 'ET-RDB 01' differ in ray floret color.

Plants of the new *Rudbeckia* can also be compared to plants of *Rudbeckia* 'Berlijn', not patented. In side-by-side comparisons conducted in Boijl, The Netherlands, plants of the new *Rudbeckia* differed from plants of 'Berlijn' in the following characteristics:

1. Plants of the new *Rudbeckia* were more compact than plants of 'Berlijn'.
2. Plants of the new *Rudbeckia* had smaller leaves than plants of 'Berlijn'.
3. Inflorescences of plants of the new *Rudbeckia* were longer lasting than inflorescences of plants of 'Berlijn'.
4. Plants of the new *Rudbeckia* had shorter and stronger peduncles than plants of 'Berlijn'.

BRIEF DESCRIPTION OF THE PHOTOGRAPHS

The accompanying photographs illustrate the overall appearance of the new *Rudbeckia* showing the colors as true as it is reasonably possible to obtain in colored reproductions of this type. Colors in the photographs may differ slightly from the color values cited in the detailed botanical description which accurately describe the colors of the new *Rudbeckia*.

The photograph on the first sheet comprises a side perspective view of a typical flowering plant of 'ET-RDB 02' grown in a container.

The photograph on the second sheet is a close-up view of typical inflorescences of 'ET-RDB 02'.

DETAILED BOTANICAL DESCRIPTION

The aforementioned photographs and following observations, measurements and values describe plants grown in containers during the spring in an outdoor nursery in Boijl, The Netherlands and under cultural conditions typical of commercial *Rudbeckia* production. During the production of the plants, day temperatures averaged 16° C. and night temperatures averaged 10° C. Plants were 15 weeks old when the photographs and the detailed description were taken. In the following description, color references are made to The Royal Horticultural Society Colour Chart, 2001 Edition, except where general terms of ordinary dictionary significance are used.

Botanical classification: *Rudbeckia hirta*×*Echinacea purpurea* 'ET-RDB 02'.

Parentage:

*Female, or seed, parent*.—Proprietary selection of *Rudbeckia hirta* identified as code number 7-357, not patented.

*Male, or pollen, parent*.—Proprietary selection of *Echinacea purpurea* identified as code number 124-6, not patented.

Propagation:

*Type*.—By tissue culture.

*Time to initiate roots*.—About seven to eight days at temperatures about 15° C. to 20° C.

*Time to produce a rooted young plants*.—About four weeks at temperatures about 15° C. to 20° C.

*Root description*.—Medium in thickness; fleshy; color, close to 162C.

*Rooting habit*.—Freely branching; medium density.

Plant description:

*Plant and growth habit*.—Herbaceous perennial; compact, upright to outwardly spreading and mounded plant habit; strong and freely branching growth habit with about numerous lateral branches, dense and bushy appearance; vigorous growth habit; medium growth rate.

*Plant height*.—About 60 cm to 70 cm.

*Plant width*.—About 40 cm to 50 cm.

*Lateral branches* (*flowering stems*).—Length: About 10 cm to 30 cm. Diameter: About 4 mm to 6 mm. Internode length: About 1 cm to 2.5 cm. Angle: Upright to outwardly spreading. Strength: Strong. Texture: Pubescent. Color: Close to 144A.

Foliage description:

*Arrangement*.—Alternate or opposite, simple; sessile.

*Length*.—About 10 cm to 20 cm.

*Width*.—About 2 cm to 5 cm.

*Shape*.—Oblanceolate.

*Apex*.—Acute to acuminate.

*Base*.—Attenuate to acute.

*Margin*.—Dentate; undulate.

*Texture, upper and lower surfaces*.—Pubescent; rough.

*Venation pattern*.—Pinnate.

*Color*.—Developing and fully expanded leaves, upper surface: Close to 137A; venation, close to 142C. Developing and fully expanded leaves, lower surface: Close to 138A; venation, close to 142C.

Inflorescence description:

*Form and arrangement*.—Single-type inflorescence form with elliptic-shaped ray florets and tubular disc florets; inflorescences borne on terminal and axillary peduncles above and beyond the foliar plane; ray and disc florets arranged acropetally on a capitulum.

*Fragrance*.—None detected.

*Flowering season*.—Plants begin flowering about ten weeks after planting; long flowering period, plants flower continuously from mid-July until the end of October in The Netherlands.

*Inflorescence longevity*.—Good postproduction longevity with inflorescences lasting about eight to ten weeks on the plant; inflorescences persistent.

*Quantity of inflorescences*.—Freely flowering habit, typically more than 50 inflorescences developing per plant.

*Inflorescence buds*.—Height: About 5 mm to 10 mm. Diameter: About 1 cm. Shape: Oblate. Color: Close to 142C.

*Inflorescences*.—Diameter: About 7 cm to 10 cm. Depth (height): About 5 cm to 7 cm. Diameter of disc: About 1.5 cm to 2.5 cm. Receptacle height: About 1 cm to 2 cm. Receptacle diameter: About 7 mm to 12 mm.

*Ray florets*.—Number of ray florets per inflorescence: About 14 to 22 arranged in one or two whorls. Length: About 2.5 cm to 4.5 cm. Width: About 1 cm to 1.5 cm. Shape: Elliptic. Apex: Emarginate. Base: Acute. Margin: Entire. Texture, upper surface: Smooth, glabrous. Texture, lower surface: Rough, glabrous. Color: When opening, upper surface: Close to 9A. When opening, lower surface: Close to 1B. Fully opened, upper surface: Ground color, close to 9A; towards the apex, overlain with close to 172B; towards the base, overlain with close to 187A; venation, similar to lamina colors; with development becoming closer to 172B. Fully opened, lower surface: Close to 6A; venation, close to 6A.

*Disc florets*.—Arrangement: Numerous disc florets massed at center of receptacle. Length: About 2 cm to 3 cm. Width: About 1 mm to 2 mm. Shape: Tubular, elongated. Apex: Five-pointed. Color, immature: Close to N186A. Color, mature: Close to N186A.

*Phyllaries*.—Number of phyllaries per inflorescence: About 20 to 30 in about three whorls. Length: About 1 cm to 2.5 cm. Width: About 2 mm to 5 mm. Shape: Lanceolate. Apex: Acute. Base: Fused. Margin: Entire; undulate. Texture, upper and lower surfaces: Rough, pubescent. Color, upper surface: Close to 143A. Color, lower surface: Close to 143B.

*Reproductive organs*.—Androecium (present on ray and disc florets): Quantity per floret: Numerous. Filament length: About 1 mm to 2 mm. Filament color: Close to N186A. Anther shape: Round. Anther length: About 1 mm to 2 mm. Anther color: Close to N186A. Pollen amount: Abundant. Pollen color: Close to 200B. Gynoecium (present only on disc florets): Pistil length: About 2 mm to 3 mm. Stigma shape: Two-parted. Stigma color: Close to 200B. Style length: About 1 mm to 2 mm. Style color: Close to 200B.

*Seeds and fruits*.—Seed and fruit production has not been observed on plants of the new *Rudbeckia*.

Disease & pest resistance: Resistance to pathogens and pests common to *Rudbeckia* plants has not been observed on plants of the new *Rudbeckia*.

Garden performance: Plants of the new *Rudbeckia* have been observed to have good garden performance and to tolerate wind, rain and temperatures from about −20° C. to about 40° C.

It is claimed:

1. A new and distinct *Rudbeckia* plant named 'ET-RDB 02' as illustrated and described.

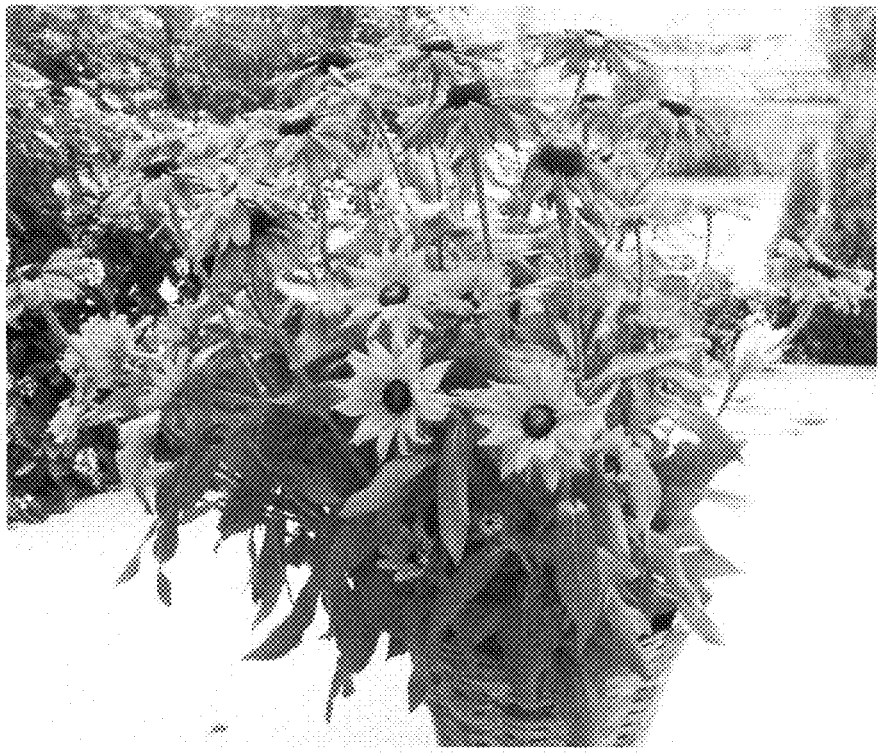

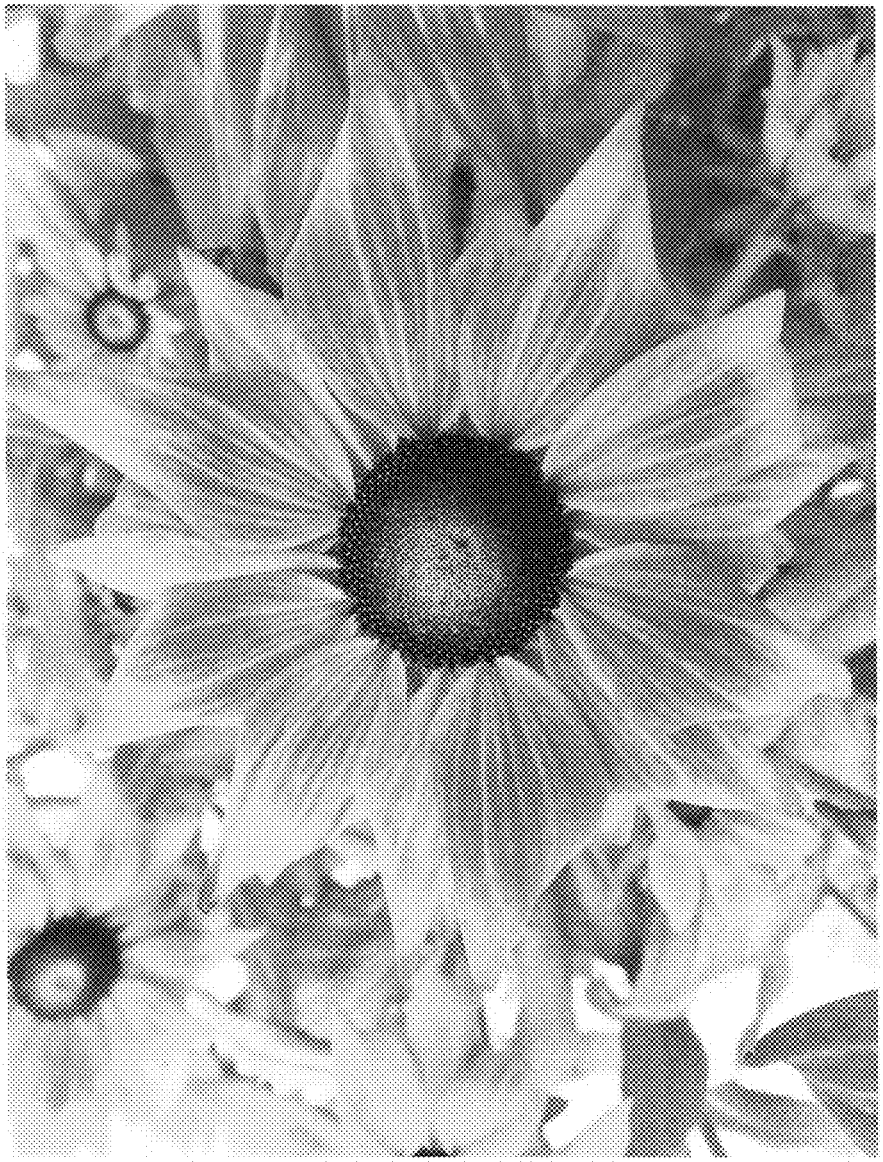

* * * * *